United States Patent
Nam et al.

Patent Number: 5,444,251
Date of Patent: Aug. 22, 1995

[54] DIAMOND RADIATION DETECTOR ELEMENT

[76] Inventors: Tom L. Nam, 114-6th Avenue, Bez Valley, Johannesburg, Transvaal; Shawn Araikum, 55 Hugo Road, Sydenham, Durban, Natal; Rex J. Keddy, 3 Bevan Road, Rivonia, Sandton, Transvaal, all of South Africa

[21] Appl. No.: 204,985

[22] Filed: Mar. 2, 1994

[30] Foreign Application Priority Data

Mar. 2, 1993 [ZA] South Africa ............... 93/1478

[51] Int. Cl.$^6$ ............................................. G01T 1/202
[52] U.S. Cl. .................................. 250/361 R; 250/362
[58] Field of Search ............... 250/361 R, 362, 363.01, 250/483.1

[56] References Cited

U.S. PATENT DOCUMENTS

| | | |
|---|---|---|
| 3,824,680 | 7/1974 | Kozlov et al. |
| 4,045,674 | 8/1977 | Vermeulen et al. |
| 4,465,932 | 8/1984 | Burgemeister |
| 4,754,140 | 6/1988 | Nam et al. |
| 4,833,328 | 5/1989 | Prins et al. |
| 4,888,483 | 12/1989 | Grobbelaar |
| 5,012,108 | 7/1991 | Nam et al. |
| 5,097,133 | 3/1992 | Nam et al. |
| 5,128,546 | 7/1992 | Nam et al. |

FOREIGN PATENT DOCUMENTS

0479625 10/1991 European Pat. Off.
0560627  3/1993 European Pat. Off.

*Primary Examiner*—Paul M. Dzierzynski
*Assistant Examiner*—Richard Hanig
*Attorney, Agent, or Firm*—Scully, Scott, Murphy & Presser

[57] ABSTRACT

The invention provides a method of detecting and monitoring ionizing radiation such as nuclear radiation. The method comprises providing a diamond radiation sensor element having a nitrogen concentration not exceeding 20 ppm and which is optimized for phosphorescent response, and exposing it to ionizing radiation. The resulting phosphorescent response of the sensor element is then monitored, typically over a period of at least 20 seconds. The invention extends to the sensor element itself, and to apparatus employing the sensor.

19 Claims, 4 Drawing Sheets

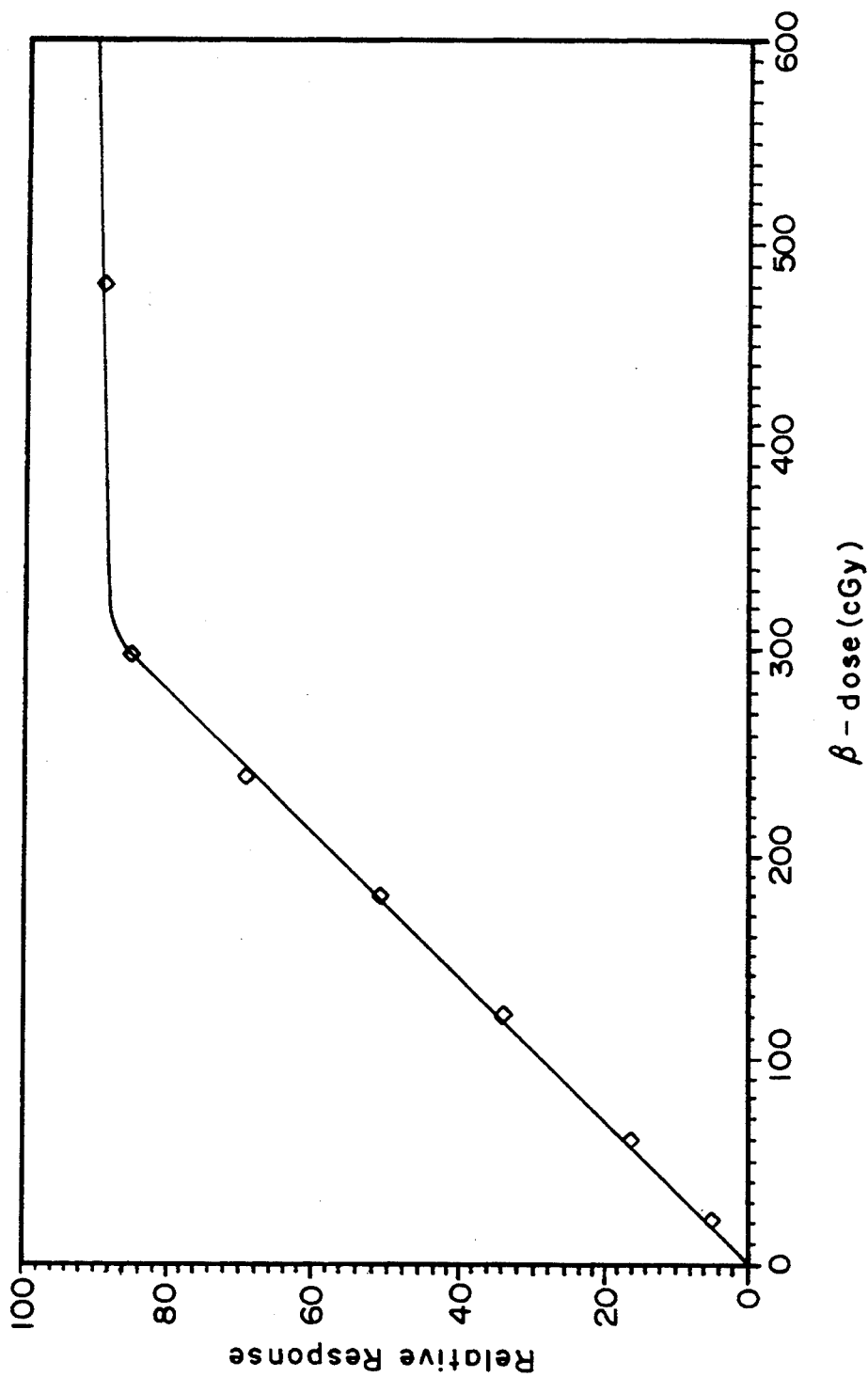

DIAMOND RADIATION DETECTOR ELEMENT

BACKGROUND OF THE INVENTION

This invention relates to a method of and apparatus for the detection and monitoring of ionizing radiation.

SUMMARY OF THE INVENTION

According to the invention a method of detecting and monitoring ionizing radiation comprises providing a diamond radiation sensor element having a paramagnetic nitrogen concentration not exceeding 20 ppm and which is optimised for phosphorescent response, exposing the sensor element to ionizing radiation, and monitoring the phosphorescent response of the sensor element due to the ionizing radiation.

Preferably, the phosphorescent response of the sensor element is monitored for a period of at least one second.

The phosphorescent response may monitored for a period of at least 20 seconds and preferably at least 60 seconds.

Light emitted by the sensor element may be amplified, with an electrical signal related thereto being generated which is representative of the intensity of the incident radiation.

The electrical signal may be integrated over a predetermined period of time.

Alternatively, the electrical signal may be displayed as a function of time.

Further according to the invention a sensor element for monitoring ionizing radiation comprises a diamond body which has a paramagnetic nitrogen concentration not exceeding 20 ppm and which is optimised for phosphorescent response.

The paramagnetic nitrogen concentration of the diamond body is preferably 10 ppm or less.

The diamond body may contain boron as an impurity. The boron concentration is preferably 20 ppm or less.

The diamond body preferably has a concentration of a Group VIII element of between 10 and 100 ppm.

The Group VIII element may comprise one or more of iron, cobalt and nickel.

The one embodiment of the method, the sensor element is formed by a high pressure, high temperature process in the presence of a catalyst comprising one or more of iron, cobalt and nickel.

In another embodiment, the sensor element is formed by a chemical vapour deposition process, during which boron is introduced in a gaseous form.

Still further according to the invention, apparatus for monitoring ionizing radiation comprises a diamond sensor element as defined above; light sensor means for detecting the phosphorescent response of the radiation sensor element; and monitoring means for translating the monitored response into an output representative of the intensity of radiation incident on the radiation sensor element.

The light sensor means may comprise an optical fibre and a photomultiplier tube.

The monitoring means may include an A/D converter, processor means for integrating an output signal and the A/D convertor over a predetermined period of time, and display means for displaying the integrated output signal.

Alternatively, the monitoring means may include an A/D convertor, processor means for generating a signal representing an output signal of the A/D convertor as a function of time, and display means for displaying the output signal.

BRIEF DESCRIPTION OF THE DRAWINGS

FIG. 5 is a graph showing the relevant phosphorescense intensity of the diamond sensor element as a function of the incident beta radiation dose.

DESCRIPTION OF AN EMBODIMENT

Phosphorescence and fluorescence are both phenomena involving the luminescense of a material, in this case a diamond body. One distinction between the two phenomena is the time in which they both occur. In a diamond, fluorescence is an immediate effect, with a delay between excitation of the diamond and the emission of light of less than $10^{-8}$s. In the case of phosphorescence, the delay between excitation and the emission of light is greater than $10^{-8}$s, and the light emission is of much longer duration and may continue for typically 90 to 150 seconds after stimulation of the diamond with radiation. Another distinction is the physical mechanism responsible for each phenomenon. In the case of fluorescence, the incident $\beta$ particle providing the stimulation lifts charge carriers from their stable state to a stimulated state, from which they eventually fall back to recombine with available holes. In falling back, they release energy in the form of visible light.

In the case of phosphorescence, the stimulated carriers fall back to an intermediate trapping level before returning to their stable state and recombining. This additional step lengthens the duration of the light output and is observed as phosphorescence, long after the stimulation ceases. Effectively, light is emitted in two stages. The existence of the intermediate trapping level is due to the presence of defects, impurities or dislocations in the diamond lattice.

Figure 1:
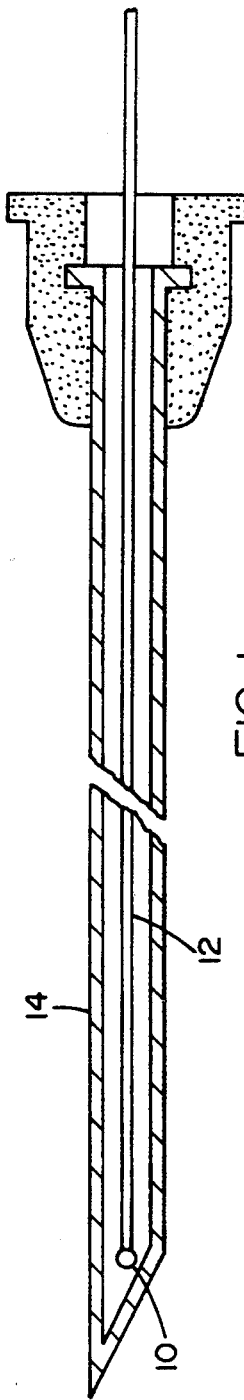
FIG. 1 is a schematic illustration of part of an apparatus for monitoring ionizing radiation according to the invention, showing a diamond sensor element mounted at the end of an optical fibre.

FIG. 1 shows a radiation sensor element 10 comprising a diamond crystal which is typically less than 1 mm in diameter, and which has a flat contact site thereon which abuts the end of an optical fibre 12 of a similar diameter. The element may be fixed to the optical fibre by adhesive, for example, or may be held mechanically against the fibre, by a heat-shrink sleeve, or by means of a cap which holds the sensor element against the optical fibre in a tube or sleeve.

The sensor element 10 and the optical fibre 12 are shown inside a metal needle 14 which can be inserted into the body of a patient. Instead of a metal needle, a flexible catheter can be used, through which the sensor element can be fed into the patient's body.

The diamond sensor element of the invention can be synthesized according to techniques well known in the art, including high pressure/high temperature methods, or by low pressure chemical vapour deposition. The concentration of paramagnetic nitrogen in the diamond should not exceed about 20 ppm and preferably should not exceed less than 10 ppm, to avoid the presence of recombination centres ("killer centres") for $\beta$ particles which effectively cut off charge carriers.

These levels can be achieved by evacuating the reaction capsule used in high pressure high temperature synthesis prior to loading of the press apparatus. In the case of vapour deposition, careful attention to the purity of the reactants and the sealing of the reactor system to the atmosphere contributes to low nitrogen concentration.

To obtain prototype diamond sensor elements, a selection was made from diamonds synthesised under high pressure, high temperature conditions (by methods known per se) in the presence of a molten metal catalyst comprising an alloy of Group VIII elements of the periodic table, including Ni/Fe and Co/Fe. It was found that diamonds having a concentration of the metal catalyst of greater than 10 ppm, and typically within the range 10 to 100 ppm, had the most suitable phosphorescence characteristics. In particular, the presence of iron in the above/mentioned range of concentrations is believed important to the performance of the diamond in this application. Atoms of iron become included in the diamond during crystal growth in the synthesis process.

It can be noted that these concentrations are approximately an order of magnitude less than those found in synthetic diamonds produced by similar high temperature, high pressure processes which are used as abrasives.

As mentioned above, the intensity of the phosphorescent response of the diamond is understood to be due to the presence of defects, impurities or dislocations in the diamond lattice. In the case of diamonds formed by high pressure, high temperature synthesis, the iron or iron alloy atoms from the catalyst used in the process function in this way. In the case of diamond synthesised by chemical vapour deposition, defects and dislocations can be caused by varying the growth conditions, and are found to occur particularly at high growth rates, in excess of 100 $\mu$m per hour.

At the preferred nitrogen concentrations, it is found that there is an increase in the trapping level concentration in the diamond compared with diamonds having a higher nitrogen concentration. It is these shallow trapping states that are effectively utilised by the incident radiation resulting in detectable phosphorescence being emitted from the diamond sensor element. The sensitivity of the sensor's phosphorescent response is further enhanced by the incorporation of suitable impurities such as boron, the presence of which is believed to give rise to temporary trapping sites which enable phosphorescence to occur. It has been found that the boron concentration should be kept below 20 ppm.

The sensor element can be doped with boron after or during manufacture thereof. For example, diborane gas can be introduced into the reaction vessel in the case of a sensor element formed by chemical vapour deposition, to dope the sensor element uniformly with boron. Alternatively, the sensor element can be doped by implantation of boron ions.

Figure 2:
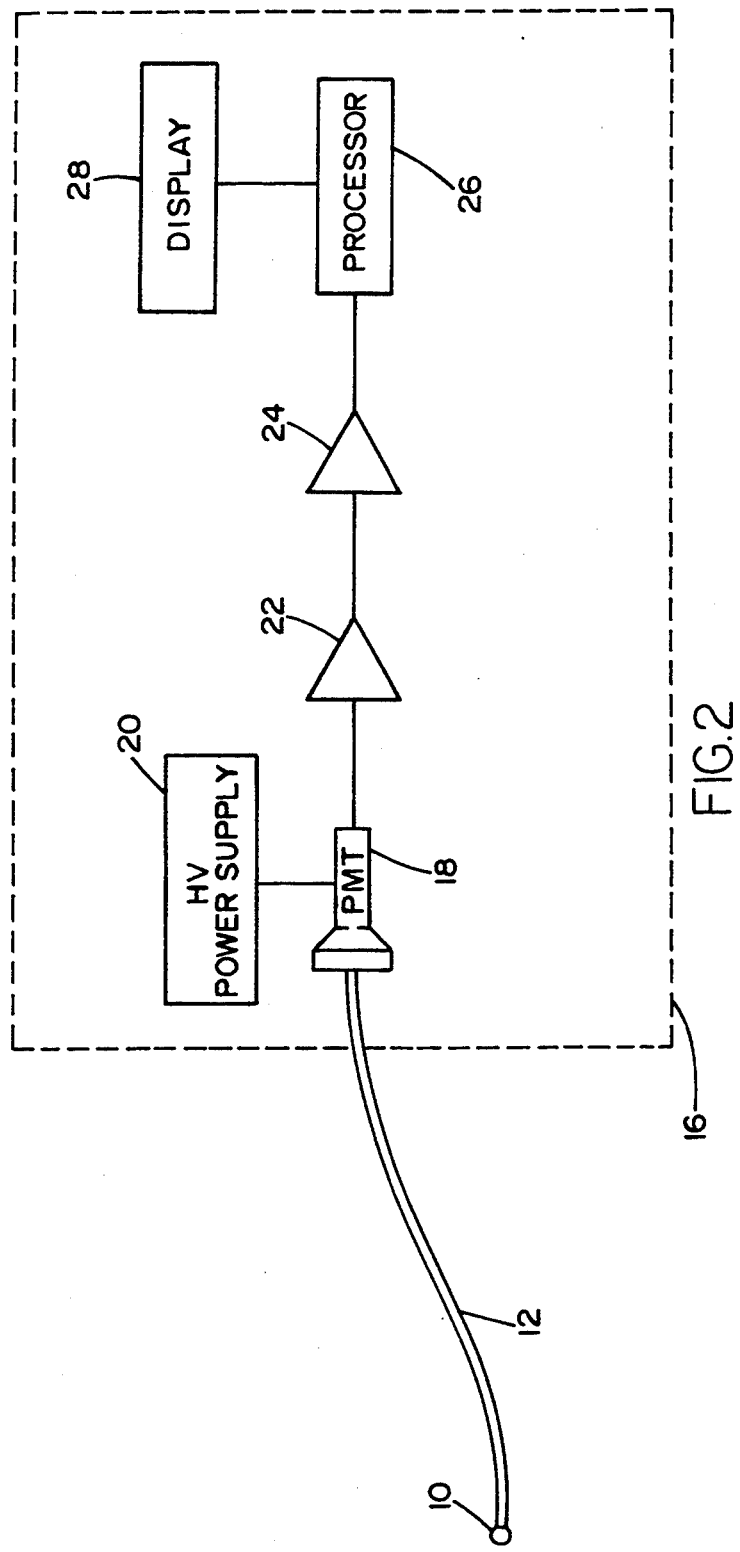
FIG. 2 is a simplified schematic block diagram showing electronic circuity of the apparatus.

FIG. 2 is a schematic illustration of the radiation sensor apparatus of the invention. The diamond sensor element 10 and the optical fibre 12 are shown schematically, and are connected to an electronic monitoring circuit 16. The circuit 16 includes a photomultiplier tube 18 (or other sensor, such as a CCD) to which the optical fibre 12 is connected and which is arranged to amplify the phosphorescent output of the diamond sensor element 10 which is transmitted via the optical fibre 12. A high voltage power supply 20 powers the photomultiplier tube 18. The photomultiplier tube 18 produces an electrical output signal proportional to the intensity of the light emitted by the diamond sensor element 10, which is amplified by a preamplifier 22 and a second amplifier 24. The output of the amplifier 24 is in turn fed to a processing circuit 26, which can translate the amplified electrical output signals of the photomultiplier tube into signals which can drive a display 28, to provide an indication of the intensity of the light output of the sensor element, and thus of the intensity of the radiation incident on the radiation element.

The processor 26 in the prototype system of the invention included an A/D convertor and a multichannel scanner operating in multiscaler mode, with the received signal from the photomultiplier tube being displayed either as an integrated count or as a function of time, with measurements for each individual time period being stored in separate bins. The total time over which the light output from the sensor element is measured can be selected arbitrarily, but will normally be at least one second, and is typically 20 seconds or more, and may be 60 seconds or more.

Each sensor element would be calibrated before use in the field, against a reference radiation source.

The radiation detector of the invention is well suited to in vivo use in the medical field, since diamond is a tissue equivalent material. Furthermore, although the phosphorescent response of diamond is temperature dependent, the thermoregulation of the human body is known to be very efficient, maintaining a temperature at around 37.5° C. Within 5 degrees on either side of this temperature, the response of the sensor, as measured by a photomultiplier tube, is substantially linear, allowing simultaneous dosage monitoring to be performed with exposure of the sensor to the radiation.

Figure 3:
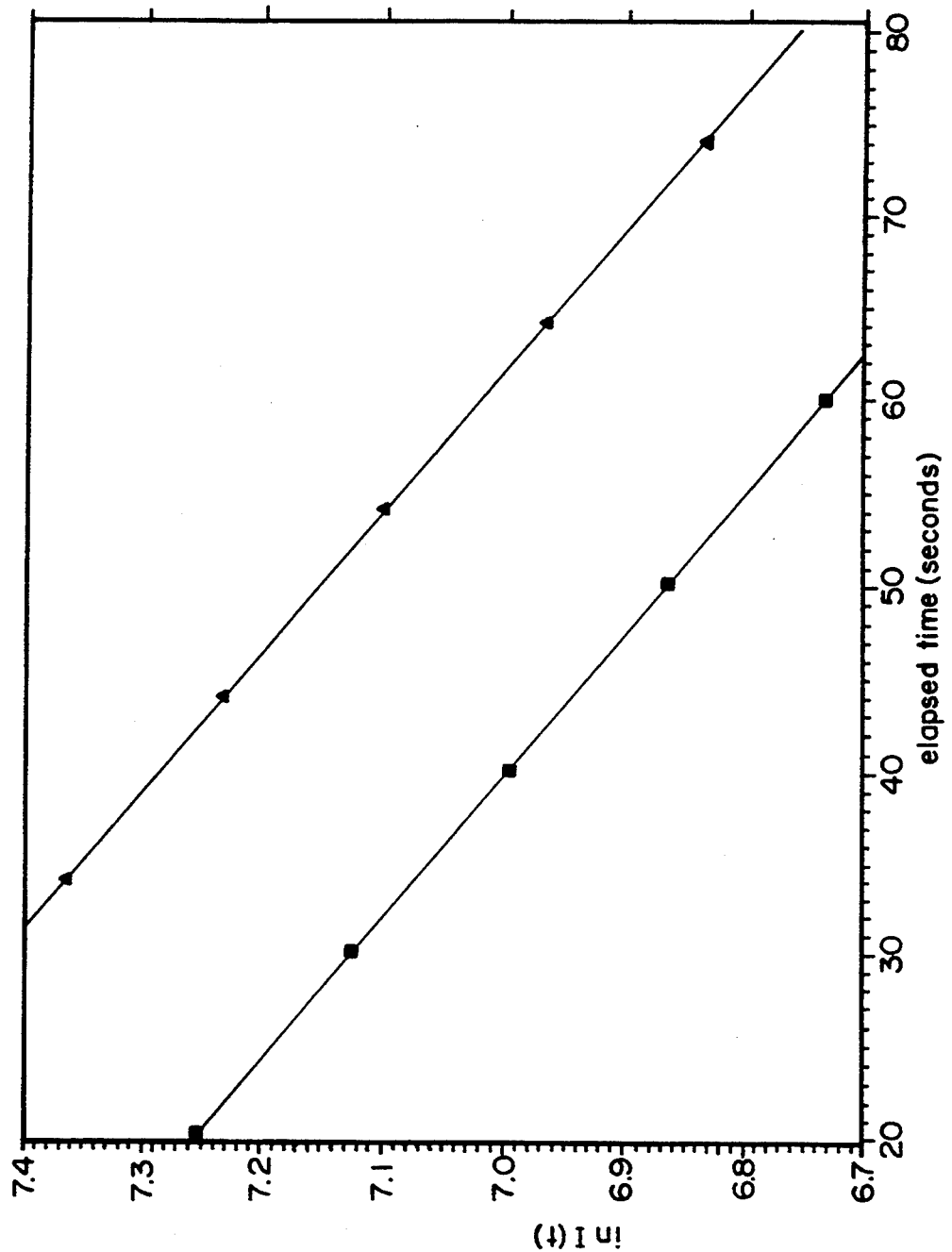
FIG. 3 is a graph showing the response of a diamond sensor element according to the invention at two different temperatures.

FIG. 3 shows the phosphorescence response of the sensor element as a function of temperature, with two sets of measurements being taken at 20° C. and 40° C. respectively. The fitted values for the decay lifetimes show a difference in value of approximately 2%, over a range which substantially exceeds the maximum possible variation in body temperature of a human patient.

Figure 4:
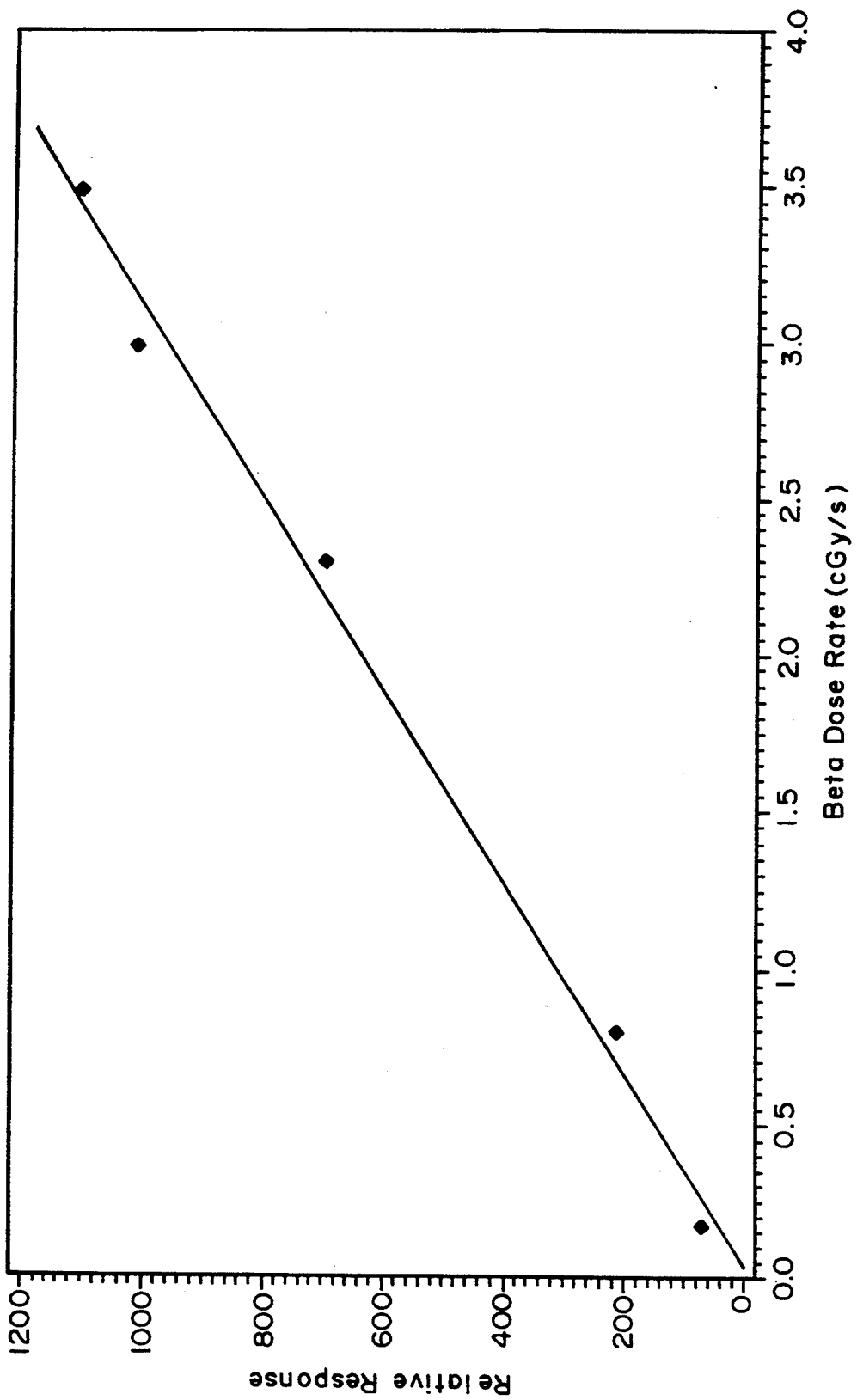
FIG. 4 is a graph showing the plot of a response of a diamond sensor element according to the invention to stimulation by beta radiation as measured by dose rate.

The graph of FIG. 4 shows the phosphorescence response of the diamond sensor element 10 used in a dose rate measuring mode. In this example, beta radiation dose rates below about 4 cGy/s were measured. These measurements were effected by placing the sensor element 10 at different distances from a $^{90}$Sr source for 30 seconds, effectively varying the dose rate applied to the sensor element, and measuring the phosphorescence response.

FIG. 5 shows the response of the sensor element 10 used as a dose meter to measure total dose, by integrating the amplified electrical output signal of the photomultiplier tube 18 over time, with greater radiation doses, up to a dose of approximately 600 cGy. It can be seen from the graph that a substantially linear response is obtained, with saturation setting in at a dose of approximately 300 cGy.

The diamond sensor element used in the above measurements was a synthetic diamond crystal of approximately 1 mm$^3$, manufactured by a high pressure/high temperature process, and selected to have paramagnetic nitrogen impurity concentration, as measured by electron spin resonance (ESR) techniques, of less than 10 ppm.

Using, for example, the isotope iridium 192 as a radiation source, and a diamond detector element of 1 mm$^3$, mounted in a suitable holder in parallel catheters drawn through or inserted into a patient's body, a direct readout of the radiation dose applied to the patient can be obtained. The diamond is linked by an optical fibre to a photomultiplier tube (PMT) connected to an electronic processor, as described above. The output from the processor gives a readout of the instantaneous radiation dose or total dose received by the patient.

We claim:

1. A method of detecting and monitoring ionizing radiation comprising providing a diamond radiation sensor element having a paramagnetic nitrogen concentration not exceeding 20 ppm and which is optimised for phosphorescent response, exposing the sensor element to ionizing radiation, and monitoring the phosphorescent response of the sensor element due to the ionizing radiation.

2. A method according to claim 1 wherein the phosphorescent response of the sensor element is monitored for a period of at least one second.

3. A method according to claim 2 wherein the phosphorescent response is monitored for a period of at least 20 seconds.

4. A method according to claim 3 wherein the phosphorescent response is monitored for a period of at least 60 seconds.

5. A method according to claim 1 wherein light emitted by the sensor element is amplified and an electrical signal related thereto is generated which is representative of the intensity of the incident radiation.

6. A method according to claim 5 wherein the electrical signal is integrated over a predetermined period of time.

7. A method according to claim 5 wherein the electrical signal is displayed as a function of time.

8. A sensor element for monitoring ionizing radiation comprising a diamond body which has a paramagnetic nitrogen concentration not exceeding 20 ppm and which is optimised for phosphorescent response.

9. A sensor element according to claim 8 wherein the paramagnetic nitrogen concentration of the diamond body is 10 ppm or less.

10. A sensor element according to claim 8 wherein the diamond body contains boron as an impurity.

11. A sensor element according to claim 10 wherein the boron concentration is 20 ppm or less.

12. A sensor element according to claim 8 wherein the diamond body has a concentration of a Group VIII element of between 10 and 100 ppm.

13. A sensor element according to claim 12 wherein the Group VIII element comprises one or more of iron, cobalt and nickel.

14. A sensor element according to claim 13 which is formed by a high pressure, high temperature process in the presence of a catalyst comprising one or more of iron, cobalt and nickel.

15. A sensor element according to claim 8 wherein the diamond body is formed by a chemical vapour deposition process, during which boron is introduced in a gaseous form.

16. Apparatus for monitoring ionizing radiation comprising a diamond sensor element having a diamond body which has a paramagnetic nitrogen concentration not exceeding 20 ppm and which is optimised for phosphorescent response; light sensor means for detecting the phosphorescent response of the radiation sensor element; and monitoring means for translating the monitored response into an output representative of the intensity of radiation incident on the radiation sensor element.

17. Apparatus according to claim 16 wherein the light sensor means comprises an optical fibre and a photomultiplier tube.

18. Apparatus according to claim 16 wherein the monitoring means includes an A/D converter, processor means for integrating an output signal of the A/D convertor over a predetermined period of time, and display means for displaying the integrated output signal.

19. Apparatus according to claim 16 wherein the monitoring means includes an A/D convertor, processor means for generating a signal representing an output signal of the A/D convertor as a function of time, and display means for displaying the output signal.

* * * * *